(12) United States Patent
Wallace

(10) Patent No.: US 12,279,948 B2
(45) Date of Patent: Apr. 22, 2025

(54) VALVE RETENTION SUPPLEMENTED WITH A WIRE HOOP

(71) Applicant: Cephea Valve Technologies, Inc., Santa Clara, CA (US)

(72) Inventor: Daniel T. Wallace, Santa Cruz, CA (US)

(73) Assignee: Cephea Valve Technologies, Inc., Abbott Park, IL (US)

( * ) Notice: Subject to any disclaimer, the term of this patent is extended or adjusted under 35 U.S.C. 154(b) by 519 days.

(21) Appl. No.: 17/182,652

(22) Filed: Feb. 23, 2021

(65) Prior Publication Data

US 2021/0267755 A1   Sep. 2, 2021

Related U.S. Application Data

(60) Provisional application No. 62/982,304, filed on Feb. 27, 2020.

(51) Int. Cl.
*A61F 2/24*      (2006.01)

(52) U.S. Cl.
CPC ......... *A61F 2/2409* (2013.01); *A61F 2/2418* (2013.01); *A61F 2/2436* (2013.01)

(58) Field of Classification Search
CPC .... A61F 2/2409; A61F 2/2418; A61F 2/2436; A61F 2/2433; A61F 2250/0098; A61F 2002/3008; A61F 2250/0096; A61B 2090/376; A61B 2090/3966
See application file for complete search history.

(56) References Cited

U.S. PATENT DOCUMENTS

| | | | |
|---|---|---|---|
| 2008/0015687 A1* | 1/2008 | Lashinski | A61F 2/2439 623/2.1 |
| 2015/0257879 A1* | 9/2015 | Bortlein | A61F 2/2418 623/2.11 |
| 2017/0056215 A1* | 3/2017 | Nagesh | A61F 2/856 |
| 2017/0165058 A1* | 6/2017 | Rothstein | A61F 2/243 |
| 2017/0165065 A1* | 6/2017 | Rothstein | A61F 2/2418 |
| 2017/0231757 A1* | 8/2017 | Gassler | A61F 2/2415 623/2.17 |
| 2017/0258586 A1* | 9/2017 | Bateman | A61F 2/2409 |
| 2017/0290686 A1* | 10/2017 | Sirhan | A61F 2/90 |
| 2018/0055630 A1* | 3/2018 | Patel | A61F 2/2427 |
| 2018/0271652 A1 | 9/2018 | Spence et al. | |
| 2019/0060068 A1* | 2/2019 | Cope | A61F 2/2439 |
| 2020/0000579 A1* | 1/2020 | Manash | A61F 2/2409 |

OTHER PUBLICATIONS

International Search Report including Written Opinion for PCT/US2021/019200 mailed Jun. 16, 2021; 12 pages.

\* cited by examiner

*Primary Examiner* — Sarah W Aleman
*Assistant Examiner* — Mikail A Mannan
(74) *Attorney, Agent, or Firm* — SLEMAN & LUND LLP

(57) ABSTRACT

The present disclosure provides systems and methods for a replacement mitral valve. The replacement valve may be made of a less rigid material thereby allowing the packed diameter of the replacement valve to be decreased. The less rigid replacement mitral valve may include a ventricular portion and a central portion. The ventricular portion may include a guide channel. A wire may be advanced into the guide channel. The wire in the guide channel may increase the stiffness on the ventricular side of the replacement valve. The increased stiffness may prevent the replacement valve from collapsing through a native valve annulus.

20 Claims, 6 Drawing Sheets

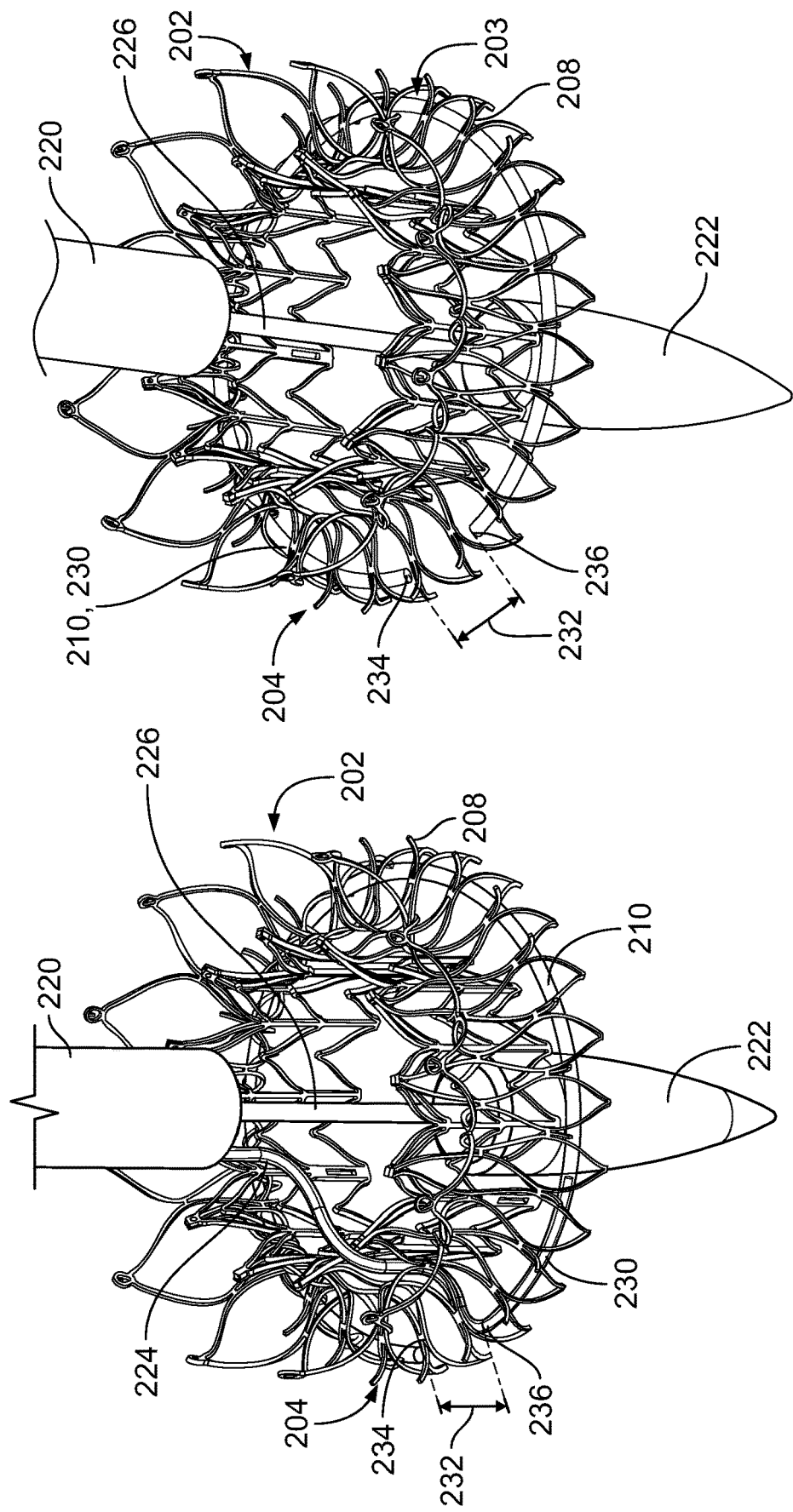

VALVE RETENTION SUPPLEMENTED WITH A WIRE HOOP

CROSS-REFERENCE TO RELATED APPLICATIONS

This application claims the benefit of the filing date of U.S. Provisional Patent Application No. 62/982,304 filed Feb. 27, 2020, the disclosure of which is hereby incorporated herein by reference.

BACKGROUND OF THE DISCLOSURE

Heart valve disease is a significant cause of morbidity and mortality. A primary treatment of this disease is valve replacement. One form of replacement device is a bioprosthetic valve. Collapsing these valves to a smaller size or into a delivery system enables less invasive delivery approaches compared to conventional open-chest, open-heart surgery. Collapsing the implant to a smaller size and using a smaller delivery system minimizes the access site size and reduces the number of potential periprocedural complications.

The size to which an implant can be collapsed is limited by the volume of materials used in the implant, the strengths and shapes of those materials, and the need to function after re-expansion. Using multiple steps and/or multiple delivery system devices may increase the time and complexity of a procedure.

BRIEF SUMMARY

One aspect of the disclosure provides for a replacement cardiac valve comprising a ventricular portion a ventricular portion having a first stiffness, the ventricular portion configured to expand from a collapsed configuration to an expanded configuration, the ventricular portion having a channel extending substantially around a circumference of the ventricular portion and a wire configured to be advanced into the channel to increase the first stiffness to a second stiffness. When the wire is advanced into the channel, the wire may form at least one loop extending through the channel.

The replacement cardiac valve may further comprise a delivery tube extending from a delivery device to a first end of the channel. The wire may be further configured to be advanced through the delivery tube and into the channel. The channel may have a first end and a second end, the first end being spaced from the second end. The channel may be positioned on a luminal surface of the ventricular portion. When the channel is wrapped substantially around the circumference of the ventricular portion, the channel creates a circle having a first diameter, the first diameter of the circle being greater than a second diameter of the native annulus.

The ventricular portion may further include a fabric cover. The channel may be positioned on a luminal surface of the ventricular portion and may be integral with the fabric cover. The channel may be a cuff coupled to the fabric cover. The ventricular portion may include a middle portion and an outflow end, the channel being located between the middle portion of the replacement cardiac valve and the outflow end. The ventricular portion may include a plurality of cells, the channel being located on a luminal surface of the plurality of cells.

Another aspect of the disclosure provides for a method of delivering a replacement cardiac valve having a collapsed configuration within a delivery device, the method comprising delivering a ventricular portion having a first stiffness from the collapsed configuration in the delivery device to a first heart chamber on a first side of a mitral valve annulus, wherein the ventricular portion expands to an expanded configuration on the first side of the mitral valve annulus, the ventricular portion having a channel wrapping substantially around a circumference of the ventricular portion and advancing a wire into the channel of the ventricular portion, wherein the ventricular portion including the wire in the channel has a second stiffness that is increased relative to the first stiffness. Advancing the wire into the channel comprises forming at least one loop extending through the channel.

The method may further comprise advancing a delivery tube from the delivery device to connect the delivery tube to a first end of the channel. The delivery tube may be removably coupled to the first end of the channel. The method may include advancing a delivery tube from the delivery device to abut a first end of the channel.

The channel may have a first end and a second end, the first end being spaced from the second end. When wrapped substantially around the circumference of the ventricular portion, the channel creates a circle having a first diameter, the first diameter being greater than a second diameter of the mitral valve annulus. Advancing the wire may comprise pushing, using a push wire in the delivery device, the wire distally though the delivery device and into the channel. The push wire may be removably coupled to the wire.

BRIEF DESCRIPTION OF THE DRAWINGS

FIG. 2C illustrates a perspective view of the of the example stent of the replacement prosthetic heart valve coupled to the deployment mechanism of the delivery device with a delivery tube according to aspects of the disclosure.

FIG. 2D illustrates a perspective view of the example deployment mechanism of the delivery device and stent with a support wire according to aspects of the disclosure.

DETAILED DESCRIPTION

The present disclosure provides for a collapsible prosthetic cardiac valve implant with reduced rigidity as compared to prior art collapsible prosthetic valves. The reduced rigidity may be accomplished by reducing the thickness of the metal used to fabricate the stent of the collapsible prosthetic cardiac valve. The disclosure further provides for a single deployment mechanism of a delivery device for deployment of the collapsible cardiac valve implant and assembly. The collapsible cardiac valve implant may collapse into a delivery sheath or system such that, due to the valve's decreased rigidity, the collapsible cardiac valve may have a decreased or minimal packed diameter as compared to a more rigid collapsible cardiac valve. Once the collapsible cardiac valve is deployed and/or expanded in the native valve annulus, the rigidity of the collapsible cardiac valve may be supplemented. According to some examples, the rigidity of the collapsible cardiac valve may be supplemented with a wire inserted into a channel extending substantially around a circumference of a ventricular portion of the collapsible cardiac valve. The rigidity of the wire may supplement the rigidity of the collapsible cardiac valve such that the ventricular portion may resist collapsing through the native valve annulus once implanted.

A minimal or decreased packing diameter of the collapsible cardiac valve may reduce the rate of vascular and cardiac complications. According to some examples, when the packed diameter of the collapsible cardiac valve is less than 8-10 mm, closure of the intra-atrial septum may not be necessary. Removing the need to close the intra-atrial septum may reduce the cost of surgery, complications arising from the surgery, and the length of the surgery.

Figure 1A:
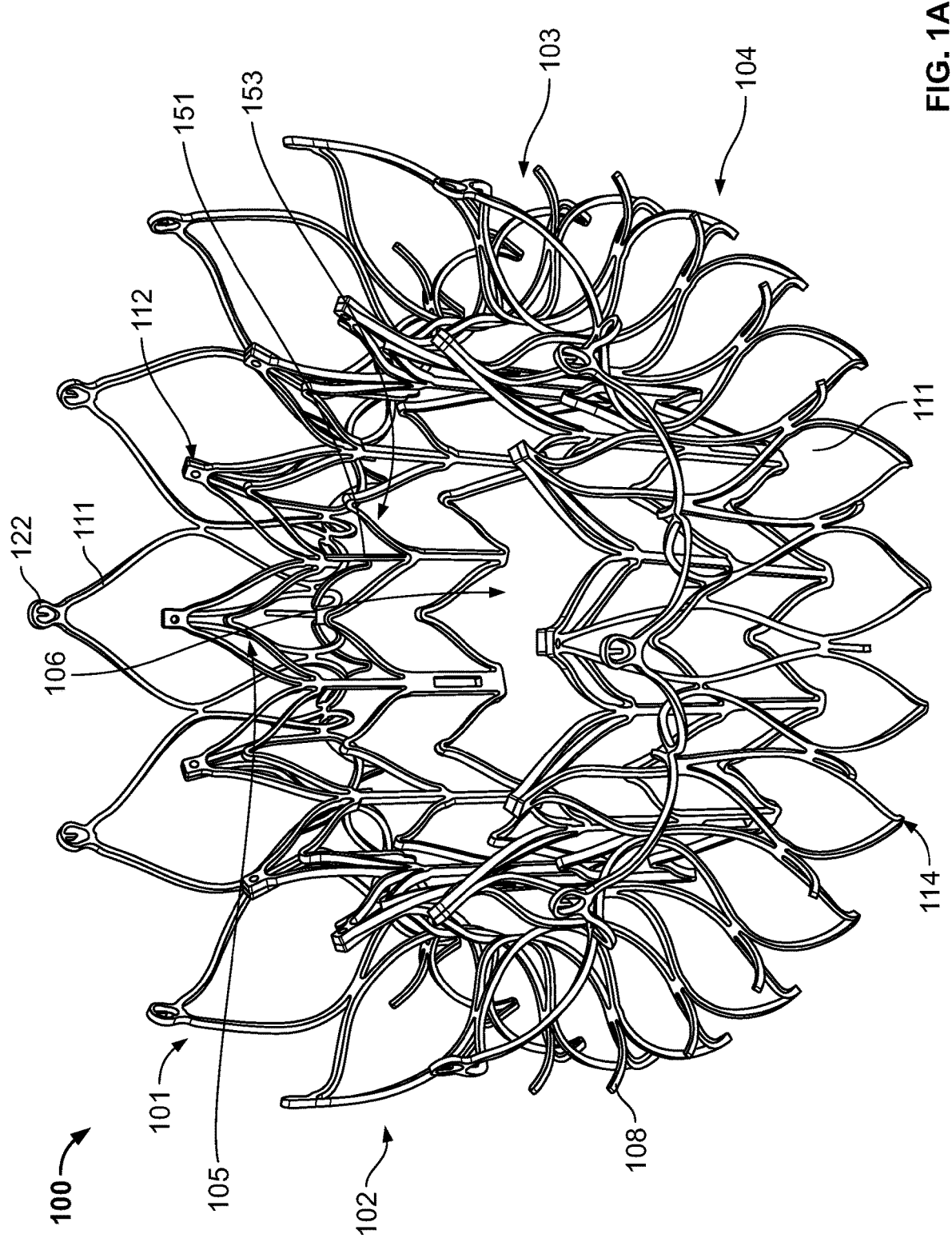
FIG. 1A illustrates a perspective view of an example stent of a replacement prosthetic heart valve including an anchor assembly and strut frame in an expanded configuration according to aspects of the disclosure.

FIG. 1A illustrates an example of a prosthetic replacement valve 100 for replacing a heart valve, and particularly atrioventricular valves such as the mitral valve or the tricuspid valve. It should be understood that replacement valve 100 would typically include the illustrated stent, one or more prosthetic leaflets that provide the valve functionality, and one or more skirts or cuffs to assist in sealing the replacement valve 100 and/or in allowing tissue ingrowth to fix the replacement valve 100 in the anatomy over time. For example, the luminal and/or abluminal surface of any stent component may include a skirt, such as a fabric skirt or a tissue skirt. However, for purposes of simplicity, the prosthetic leaflet(s) and skirt(s) are omitted from the drawings for clarity of illustration. The replacement valve 100 is illustrated in FIG. 1A in an expanded configuration. The stent of the replacement valve 100 may include an anchor assembly 101 and a strut frame 105.

Figure 1B:
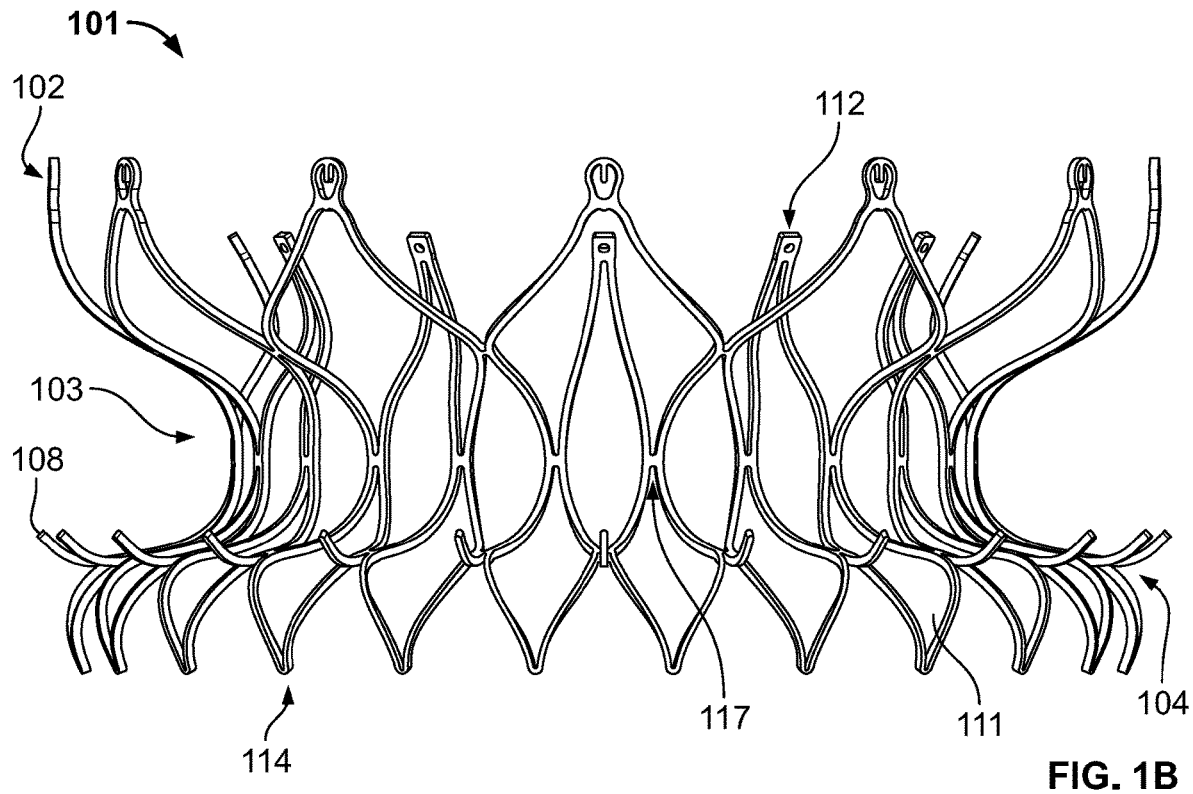
FIG. 1B illustrates a perspective view of the anchor assembly of the stent of FIG. 1A according to aspects of the disclosure.

Anchor assembly 101 is illustrated in FIG. 1B isolated from other components of the replacement valve 100. As shown in FIG. 1B, anchor assembly 101 may include an atrial portion or anchor 102, a ventricular portion or anchor 104, and a central portion 103 coupling the atrial portion to the ventricular portion. The central portion 103 may be between atrial portion 102 and ventricular portion 104. Atrial portion 102 may be configured and adapted to be disposed on an atrial side of a native valve annulus. Ventricular portion anchor 104 may be configured and adapted to be disposed on a ventricle side of the native valve annulus. The central portion 103 may be configured to be situated in the valve orifice. According to some examples, the central portion 103 may have a diameter that is substantially the same size as the native valve annulus (i.e., it is not designed to be larger than the annulus).

The atrial portion 102 may be formed as a portion of a stent or other support structure that includes or is formed by a plurality of diamond shaped cells, although other suitable cell shapes, such as triangular, quadrilateral, or polygonal may be appropriate. In some examples, the atrial portion 102 may be formed as a braided mesh, as a portion of a unitary stent, or a combination thereof. According to one example, the stent that includes the atrial portion 102 may be laser cut from a tube of nitinol and heat set to a desired shape so that the stent, including atrial portion 102, is collapsible for delivery, and re-expandable to the set-shape during deployment. The atrial portion 102 may be heat set into a suitable shape to conform to the native anatomy of the valve annulus to help provide a seal and/or anchoring between the atrial portion 102 and the native valve annulus. The heat-set atrial portion 102 may be partially or entirely covered by a cuff or skirt, on the luminal and/or abluminal surface of the atrial portion 102. The skirt may be formed of any suitable material, including biomaterials such as bovine pericardium, biocompatible polymers such as ultra-high molecular weight polyethylene, woven polyethylene terephthalate ("PET") or expanded polytetrafluoroethylene ("ePTFE"), or combinations thereof. The atrial portion 102 may include features for connecting the atrial portion to a delivery system. For example, the atrial portion 102 may include pins or tabs 122 around which sutures (or suture loops) of the delivery system may wrap.

The ventricular portion 104 may also be formed as a portion the stent or other support structure that includes or is formed of a plurality of diamond shaped cells, although other suitable cell shapes, such as triangular, quadrilateral, or polygonal may be appropriate. In some examples, the ventricular portion 104 may be formed as a braided mesh, as a portion of a unitary stent, or a combination thereof. According to one example, the stent that includes the ventricular portion 104 may be laser cut from a tube of nitinol and heat set to a desired shape so that the ventricular portion 104 is collapsible for delivery, and re-expandable to the set-shape during deployment. The ventricular portion 104 may be partially or entirely covered by a cuff or skirt, on the luminal and/or abluminal surface of the ventricular portion 104. The skirt may be formed of any suitable material described above in connection with the skirt of atrial portion 102. It should be understood that the atrial portion 102 and ventricular portion 104 may be formed as portions of a single support structure, such as a single stent or braided mesh. However, in other embodiments, the atrial portion 102 and ventricular portion 104 may be formed separately and coupled to one another.

Figure 1C:
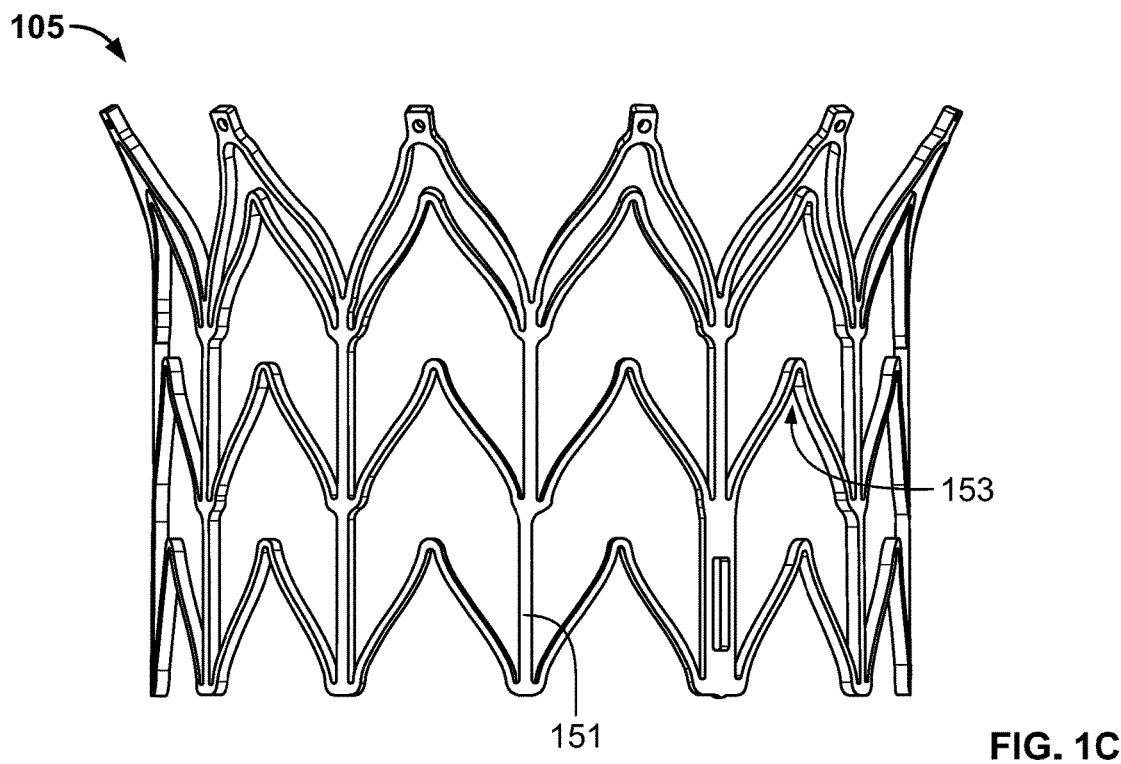
FIG. 1C illustrates a perspective view of the strut frame of the stent of FIG. 1A according to aspects of the disclosure.

As illustrated in FIG. 1A, the strut frame 105 may be positioned radially within the anchor assembly 101. As shown in FIG. 1C, the strut frame 105 may include a plurality of axially or longitudinally extending struts 151 and interconnecting v-shaped members 153. According to some embodiments, the strut frame 105 may have more or fewer v-shaped members 153 extending circumferentially around the diameter thereof than the number of cells 111 of the anchor assembly 101, such as double or half the number. In some examples, the strut frame 105 may flare radially outwards at the atrial end, e.g., to conform to the flare of the atrial anchor 102. One or more prosthetic leaflets may be coupled to the strut frame 105 to form a prosthetic valve assembly, the prosthetic valve assembly configured to allow unidirectional flow of blood through the prosthetic valve assembly from the atrial end toward the ventricular end of the replacement valve 100.

The anchor assembly 101 and/or strut frame 105 may be made of, or partially made of, a super elastic material such as nitinol. According to some examples, other biocompatible metals and metal alloys may be suitable. For example, super elastic and/or self-expanding metals other than nitinol may be suitable, while still other metals or metal alloys such as cobalt chromium or stainless steel may be suitable, particularly if the stent or support structure is intended to be balloon expandable. In some examples, the anchor assembly 101 and/or strut frame 105 may be laser cut from one or more tubes, such as a shape memory metal tube. The shape memory metal tube may be nitinol or any other bio-compatible metal tube. For example, the anchor assembly 101 may be laser cut from a first hypotube while the strut frame 105 may be laser cut from a second hypotube of smaller diameter. The anchor assembly 101 may be cut, for example, from a 9-12 mm diameter tube, such as a 10 mm tube, while the strut frame 105 can be cut, for example, from a 7-9 mm diameter tube, such as an 8 mm tube. The anchor assembly 101 may be cut from a tube having a smaller diameter, such as 6-8 mm, or a tube having a larger diameter, such as 13-15 mm. In some examples, the strut frame 105 may be cut from a tube having a smaller diameter, such as 4-6 mm, or from a tube having a larger diameter, such as 10-12 mm. Thus, the ranges and diameters provided herein are merely examples and are not meant to be limiting.

The replacement valve 100 may be adapted to expand from a collapsed or constrained configuration to an expanded configuration. According to some examples, the replacement valve 100 may be adapted to self-expand. In some examples, the replacement valve 100 may partially self-expand and partially expand by non-self-expanding influences (e.g., a balloon), or it may be fully balloon-expandable. The replacement valve 100 may be in the collapsed configuration during delivery. The replacement valve 100 may be expanded during deployment from a delivery device once the delivery device is positioned within or adjacent the native valve annulus. In the expanded configuration, the atrial anchor 102 and ventricular portion 104 may extend radially outward from a central longitudinal axis of the replacement valve and/or central portion 103, and may be considered to flare outward relative to the central longitudinal axis of the replacement valve and/or central portion 103. The atrial anchor 102 and ventricular portion 104 may be considered flanged relative to central portion 103. The flared configuration of atrial and ventricular portions 102, 104 relative to central portion 103 is described in the context of a side view of the anchor assembly, as can be best seen in FIG. 1B. In some embodiments, the flared configuration of the two anchors 102, 104 and the central portion 103 may define a general hour-glass shape in a side view of the anchor assembly 101. That is, the anchors 102, 104 may be flared outwards relative to the central portion 103 and then curved or bent to point at least partially back in the axial direction. It should be understood, however, that an hour-glass configuration is not limited to symmetrical configuration.

The anchor assembly 101 may be configured to expand circumferentially and foreshorten axially as the replacement valve 100 expands from the collapsed delivery configuration to the expanded treatment configuration. As described herein, the anchor assembly 101 may define a plurality of cells 111. Each of the plurality of cells 111 may be configured to expand circumferentially and foreshorten axially upon expansion of the anchor assembly 101. As shown, the cells 111 may each be diamond-shaped. Further, the cells 111 may be interconnected and configured such that every diamond apex 117 is connected to another diamond apex 117 except at the atrial or ventricular tips 112, 114 of the assembly 101. The anchor assembly 101 may include, for example, three circumferential rows of diamond cells 111. For example, the atrial portion 102 may comprise one row of diamond-shaped cells 111 extending circumferentially, the central portion 103 may comprise one row of diamond-shaped cells 111 extending circumferentially, and the ventricular portion 104 may comprise one row of diamond-shaped cells extending circumferentially 111. According to some examples, the atrial portion may comprise two rows of cells, the central portion may comprise three rows of cells, and the ventricular portion may comprise one row of cells. In some examples anchor assembly may include two circumferential rows of diamond cells 111 such that the atrial portion 102 may comprise one row and the ventricular portion may comprise one row. There may be any number of rows of cells in each portion and, therefore, the examples provided herein are not meant to be limiting.

The strut frame 105 may be configured to expand circumferentially while maintaining the same axial dimension (i.e., be non-foreshortening) as the replacement valve 100 expands from the collapsed delivery configuration to the expanded configuration. By being non-foreshortening, the strut frame 105 may prevent strain from being placed on the leaflets during delivery and/or packing. Thus, while the anchor assembly 101 may be designed to be foreshortening, the strut frame 105 may be designed so as to be substantially non-foreshortening.

The strut frame 105 and the anchor assembly 101 may be coupled together with coupling members, such as rivets. In some embodiments, not shown, the atrial tips of the strut frame 105 may be coupled to the coupling tips 112 of the anchor assembly 101. In examples where there are fewer v-shaped members 153 in strut frame 105 than number of cells 111 in anchor assembly 101 (as shown in FIG. 1B), the strut frame 105 may be attached to every other atrial tip 112 on the anchor assembly 101.

The radially inner surfaces of strut frame 105 may define the perimeter of a central opening 106. One or more prosthetic leaflets, which are not shown in FIGS. 1A-1B for clarity, may be secured to the strut frame 105 and may be disposed at least partially in the central opening 106. The leaflets may be configured to coapt with one another to allow unidirectional blood flow through the prosthetic valve assembly.

In some embodiments, the valve 100 may include retention features 108, such as hooks or barbs, to help anchor the assembly in the native valve orifice. As shown in FIGS. 1A and 1B, the retention features 108 may be on the located where two adjacent cells of the ventricular portion 104 intersect. According to some examples, the retention features 108 may extend radially outwardly from surface of the ventricular portion 104 that will abut the surface of the native valve annulus facing the ventricle, with free ends thereof pointing toward the atrial portion 102. For example, the retention features 108 may secure the ventricular portion 104 to a location in the ventricle, which may help resist migration of the replacement valve 100 toward the atrium when the replacement valve 100 is implanted. In some examples, the retention features 108 may be configured to engage with the ventricular side of a native mitral valve annulus when the ventricular portion 104 is in the expanded configuration.

The packed diameter of the replacement valve may be limited by a number of factors, such as the packed volume of fabric, metal, and tissue, the packing and unpacking forces that the delivery system can apply, the strain in the metal when compressed from a deployed state to a packed state, etc. To decrease the packed diameter of the replacement valve for delivery, the rigidity of the replacement valve structure may be decreased. Decreasing the rigidity of the anchor assembly, and therefore the replacement valve, may be accomplished by using less material to form the anchor assembly, using thinner materials to form the anchor assembly, using a more flexible material to form the anchor assembly, etc. According to some examples, a less rigid replacement valve may be packed to a smaller diameter or reduced profile as the packing strains on the anchor assembly may be lower. Decreasing the rigidity of the replacement valve may allow the replacement valve to be packed to a smaller diameter at a lower force compared to an otherwise similar but more rigid replacement valve. In some examples, decreasing the rigidity of the replacement valve maybe allow the replacement valve to be unpacked at a lower force during delivery.

The anchor assembly described herein may comprise less metal or material than typical replacement valves and may therefore be more flexible and may more easily collapse into a delivery configuration compared to typical replacement valves. For example, a typical ventricular portion may have a thickness of 0.4 mm to 0.44 mm to provide adequate retention force in the absence of a supplemental wire hoop. With the addition of the wire hoop to supplement the retention force, the ventricular portion may be thinned by 0.1 mm, such that its thickness may be between 0.3 mm to 0.34 mm. In some examples, the ventricular portion may be thinned by 0.13 mm, 0.08 mm, etc. Thus, thinning the ventricular portion by 0.1 mm is merely exemplary. Thinning the metal of the ventricular portion may decrease the packed volume and, therefore, the packed diameter. According to some examples, thinning the metal of the ventricular portion may cause a decrease in packing force. A decrease in packing force may reduce the strain on the metal when it is being compressed from a deployed state to a packed state. At the same time, the replacement valve described herein may maintain this flexibility in the expanded configuration. To buttress the anchor assembly, the surgeon can increase the rigidity of the replacement valve by inserting a wire hoop. By bolstering the rigidity of the replacement valve, the replacement valve may obtain adequate valve retention within the patient's heart. According to some examples, the rigidity of the replacement valve may be increased by inserting a wire circumferentially around at least a portion of the ventricular portion of the replacement valve. In some examples, the wire may be inserted into a tube or channel located in the ventricular portion of the replacement valve. The wire may prevent the ventricular portion from collapsing through the native valve annulus.

Figure 1D:
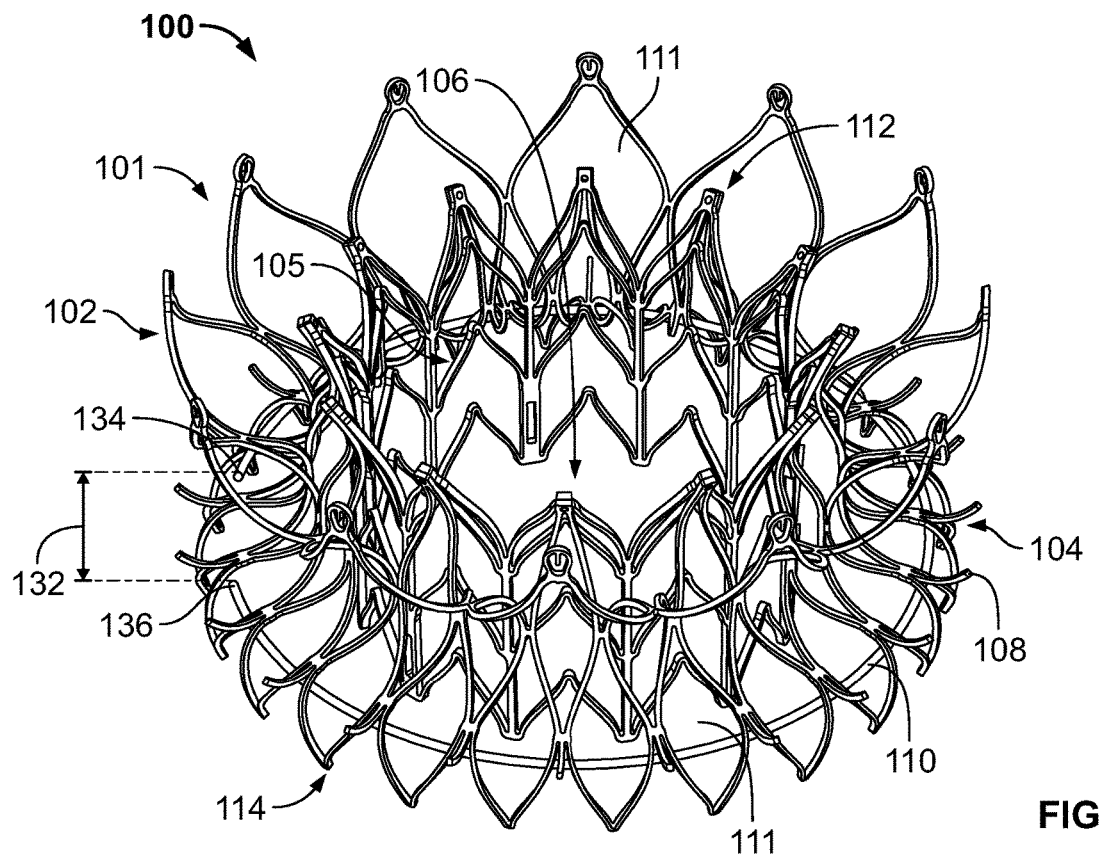
FIG. 1D illustrates a perspective view of the stent of FIG. 1A including a guide channel according to aspects of the disclosure.

FIG. 1D illustrates the example replacement valve including a guide channel 110. The guide channel 110 may be part of a fabric cover (not shown). The guide channel 110 may extend substantially around a circumference of the ventricular portion 104. For example, the guide channel 110 may form a substantially circular shape which can be a complete circle or an incomplete circle, such as a C-shaped with a gap between the first and second ends of the channel 110. The first end 134 of the guide channel 110 may be spaced from the second end 136 of the guide channel 136. The space between the first end 134 and second end 136 may define a gap or opening 132. The circular shape created by guide channel 110 may have a diameter greater than the diameter of the mitral valve annulus. Therefore, once a wire is inserted into the guide channel 110, the rigidity of the ventricular portion 104 in combination with the wire inserted therethrough may prevent the ventricular portion 104 from collapsing through the mitral valve annulus.

Figure 1E:
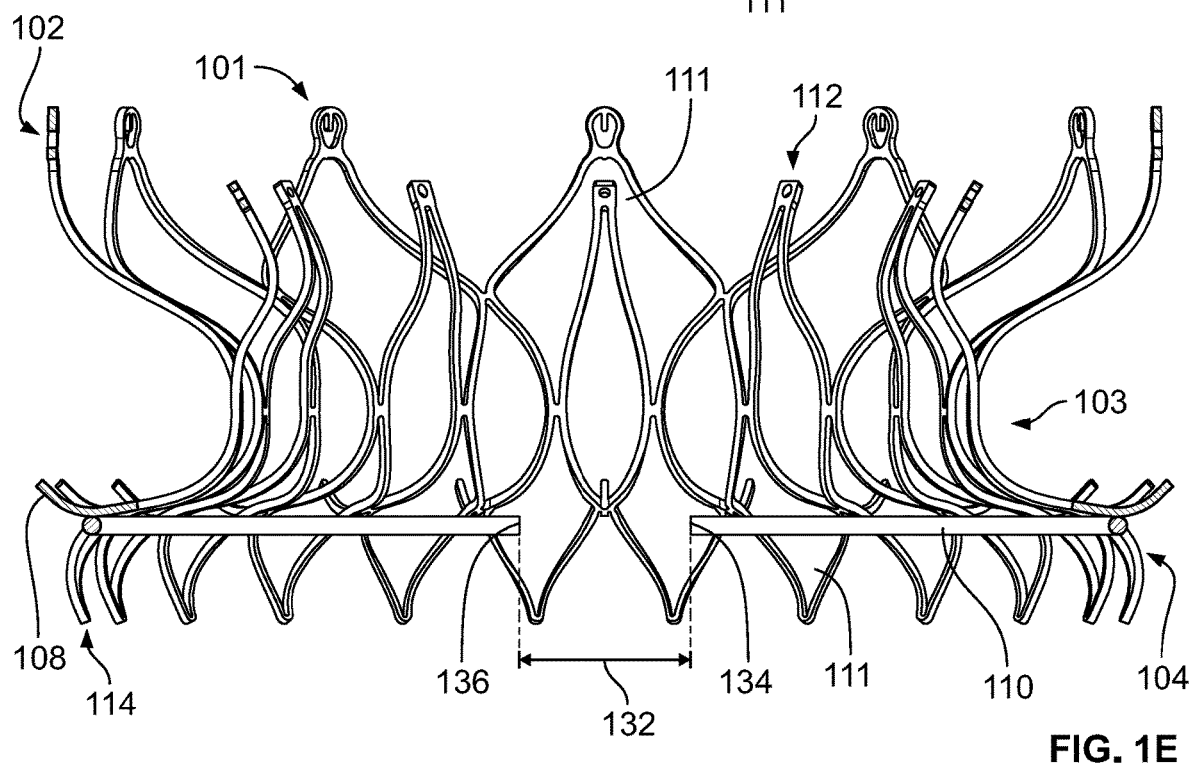
FIG. 1E illustrates a cross-section of the anchor assembly of FIG. 1B including the guide channel according to aspects of the disclosure.

The guide channel 110 may be located on a luminal surface of the ventricular portion 104. As shown in FIGS. 1D and 1E, the guide channel 110 may be located closer to the ventricular tips 114 than central portion 103 of the replacement valve when the replacement valve is in the expanded condition. However, this is merely one example and is not meant to be limiting. For example, the guide channel 110 may be located at any position along the luminal surface of ventricular portion 104 between the central portion 103 of the replacement valve and the ventricular tips 114. According to some examples, the guide channel 110 may be located on the plurality of cells 111 of the ventricular portion 104 closest to the outflow end of the replacement valve. In some examples, the guide channel 110 may be additionally or alternatively be located on the atrial portion 102 of the replacement valve. However, due to the typically increased pressure experienced by the ventricular portion of the replacement valve, there may be more need to have the guide channel 110 located on the ventricular portion 104 such that the replacement valve may better maintain its position within the native valve annulus. For example, when the ventricular portion 104 is made thinner than would normally be required, the wire within guide channel 110 may provide additional reinforcement or rigidity to the ventricular portion 104 such that the ventricular portion 104 does not collapse through the annulus.

The guide channel 110 may be defined by a cuff coupled to the skirt and/or the ventricular portion 104 of anchor assembly 101. The cuff may be, for example, a separate tube of the fabric, or other material, that is coupled to the skirt. In some examples, the guide channel 110 may be integral with the skirt. In other words, a skirt similar to those described above may be modified to define the guide channel 110 within the skirt. According to some examples, the guide channel 110 may be defined by polymer tubing. The polymer tubing may be coupled to the skirt and/or the ventricular portion 104 of anchor assembly 101. In some examples, the polymer tubing may be housed or positioned within the skirt. The polymer tubing may be formed of any suitable polymer including, for example, polyimide or polyether block amide ("PEBA"). According to some examples, the polymer tubing may be made of other types of bio-compatible polymer. And in still further embodiments, the tubing or other structure that defines the guide channel 110 may be formed of any other suitable biocompatible material.

Additional features and example replacement valves may be described in International application number PCT/US2018/014902, filed Jan. 23, 2018, and titled "REPLACEMENT MITRAL VALVES," which are incorporated is reference herein.

Figure 2A:
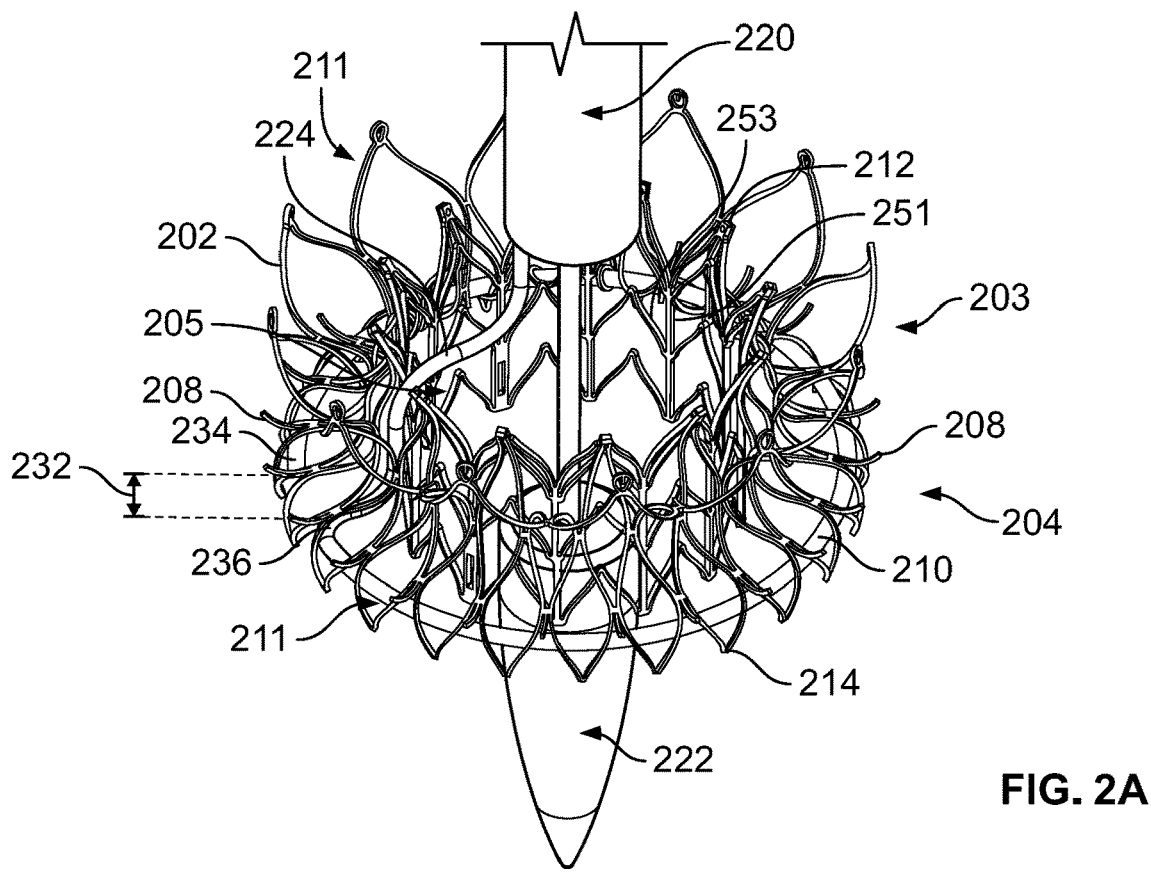
FIG. 2A illustrates a perspective view of an example stent of a replacement prosthetic heart valve coupled to a deployment mechanism of a delivery device according to aspects of the disclosure.
Figure 2B:
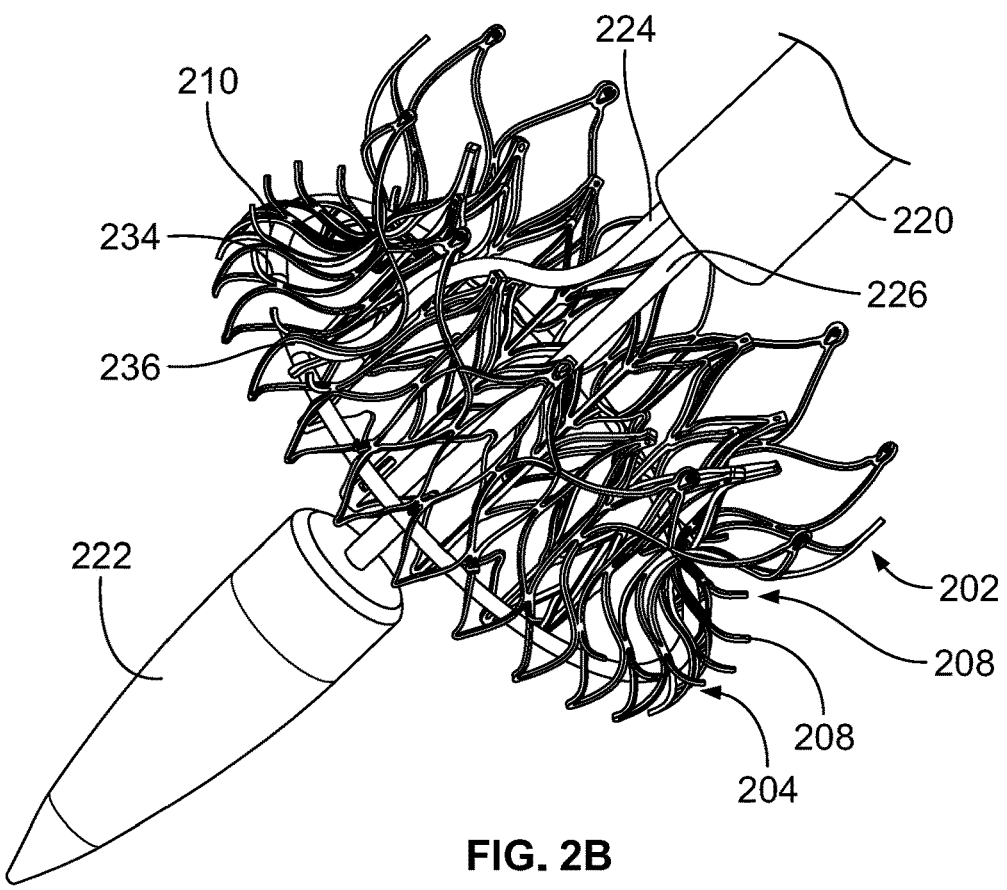
FIG. 2B illustrates an additional perspective of FIG. 2A according to aspects of the disclosure.

FIGS. 2A-2E illustrate a sequence of a wire being inserted into a channel on a ventricular portion of an example replacement valve to increase the rigidity of the replacement valve. For example, The replacement valve shown in FIGS. 2A-2E is similar to the replacement valve illustrated in FIGS. 1A and 1B and, therefore, may have corresponding reference numbers. As shown in FIGS. 2A and 2B, the replacement valve may be an atrial portion 202, a central portion 203, and a ventricular portion 204. Atrial portion 202 may be configured and adapted to be disposed on an atrial side of a native valve annulus. Ventricular portion 204 may be configured and adapted to be disposed on a ventricle side of the native valve annulus. The central portion 203 may be between the atrial portion 202 and ventricular portion 204. The central portion 203 may be configured to be situated in the valve orifice.

The atrial portion 202 may include a plurality of cells. For example, the cells 211 may be diamond shaped, although other suitable shapes, such as triangular, quadrilateral, or polygonal may be appropriate. The ventricular portion 204 may include a plurality of cells. Similar to the cells of the atrial portion, the cells 211 may be diamond shaped, although other shapes may be appropriate. The cells 211 may be interconnected and configured such that every diamond apex is connected to another diamond apex except at the atrial or ventricular tips 212, 214.

The ventricular portion 204 may include a plurality of retention features 208. The retention features 208 may be, for example, barbs or hooks. The retention features 208 may extend radially outwardly from a surface of the ventricular portion 204 that will abut the surface of the native valve annulus facing the ventricle. For example, the retention features 208 may extend from an abluminal surface of the ventricular portion 204. In some examples, the retention features 208 may be located where two adjacent cells of the ventricular portion 204 intersect. The retention features may secure the ventricular portion 204 to a location in the ventricle, which may help resist migration of the replacement valve toward the atrium when the replacement valve is implanted. In some examples, the retention features 208 may be configured to engage with the ventricular side of a native mitral valve annulus when the ventricular portion 204 is in the expanded configuration.

The replacement valve may include a strut frame positioned radially within the atrial portion 202, central portion 203, and ventricular portion 204. The strut frame 205 may include a plurality of struts 251 and interconnecting v-shaped members 253. One or more prosthetic leaflets, not shown for clarity purposes, may be coupled to the strut frame 205 to form a prosthetic valve assembly.

The replacement valve may include a fabric cover, such as a skirt or sheath, not shown for clarity purposes. The skirt may be, for example, woven PET or expanded ePTFE. According to some examples, the skirt may be made of other types of bio-compatible materials.

The fabric cover may include a guide channel 210. The guide channel 210 may be similar to the guide channel 110 described with respect to FIGS. 1D and 1E and, therefore, may have corresponding reference numbers. The guide channel 210 may extend substantially around a circumference of the ventricular portion 204. According to some examples, when guide channel 210 is wrapped substantially around the circumference of the ventricular portion 204, the guide channel 210 may form a substantially circular shape which may be complete circle or an incomplete circle. In examples where the guide channel 210 is an incomplete circle, the guide channel 210 may have a C shape with a break or opening 232 between a first end 234 and a second end 236. The first end 234 of the guide channel 210 may be spaced from the second end 236 of the guide channel 236. The space between the first end 234 and second end 236 may be opening 232. The circular shape created by guide channel 210 may have a diameter. The diameter of the circular shape created by the guide channel 210 may be greater than the diameter of the mitral valve annulus. Therefore, once a wire is inserted into the guide channel 210, the rigidity of the ventricular portion 204 in combination with a wire inserted into guide channel 210 may prevent the ventricular portion 204 from collapsing through the mitral valve annulus.

The guide channel 210 may be located on a luminal surface of the ventricular portion 204. As shown in FIGS. 2A-2E, the guide channel 210 may be located closer to the ventricular tips 214 than central portion 203 of the replacement valve. However, this is merely one example and is not meant to be limiting. For example, the guide channel 210 may be located at any position along the luminal surface of ventricular portion 204 between the central portion 203 of the replacement valve and the ventricular tips 214. According to some examples, the guide channel 210 may be located on the plurality of cells 211 of the ventricular portion 204 closest to the outflow end of the replacement valve.

The guide channel 210 may be a cuff coupled to the fabric cover. The cuff may be, for example, a separate tube of fabric, or other material, that is coupled to the skirt. In some examples, the guide channel 210 may be integral with the fabric cover. According to some examples, the guide channel 210 may be polymer tubing. The polymer tubing may be coupled or attached to the fabric cover. In some examples, the polymer tubing may be within the fabric cuff. The polymer tubing may be, for example, polyimide or Polyether block amide ("PEBA"). According to some examples, the polymer tubing may be made of other types of bio-compatible polymer.

During delivery of the replacement valve, the replacement valve may be maintained in the collapsed condition via an overlying sheath of the delivery device 220. The replacement valve may also be coupled to a deployment mechanism of delivery device 220, for example to assist with controlled deployment of the replacement valve and/or to prevent premature release of the replacement valve from the delivery device 220. The delivery device 220 may include various components, such as a handle operably coupled to one or more catheter sheaths and/or, for example an outer catheter sheath that at least partially surrounds an inner catheter shaft, with the outer sheath being translatable relative to the inner shaft. The delivery device 220 may include an atraumatic nosecone 222, which may assist with atraumatically guiding the leading end of the delivery device 220 through the patient's vasculature. The nosecone 222 may extend from the delivery device 220 via inner shaft 226, and may be fixedly coupled thereto. The delivery device 220 may deliver the replacement valve in a collapsed configuration, with the replacement valve positioned within a compartment defined between the inner shaft 226 and the overlying outer sheath while the overlying sheath is in abutment with the nosecone 222. The sutures connecting delivery device 220 to the replacement valve may remain connected to the replacement valve after the replacement valve expands to an expanded configuration, as shown in FIG. 2A. The nosecone 222 may extend through an opening between the leaflets, not shown for clarity purposes.

The ventricular portion 204 may be deployed first from delivery device 220. The tips of the atrial portion 202 may remain compressed within delivery device 220. According to one example, the wire 230 may be inserted into guide channel 210 while the atrial portion 202 remains in delivery device 220. In other examples, the atrial portion 202 may be deployed from delivery device 220 before wire 230 is inserted into guide channel 210. In such an example, the inner shaft 226 of delivery device 220 may cross the valve leaflets, thereby inducing mitral regurgitation and minimizing the pressure gradient across the valve. This may decrease the need for a high retention force prior to the removal of the delivery device 220.

In some examples, the less rigid replacement valve in the expanded configuration may maintain its position and function properly as the surgeon delivers the wire to the guide channel. For example, while the replacement valve is in the condition shown in FIGS. 2A-B, without the wire hoop inserted into guide channel 210, the replacement valve may be rigid enough to retain its position within the native valve annulus while the nosecone 222 extends through an opening between the leaflets. In other words, immediately after the replacement valve is deployed from the delivery device 220, the atrial portion 202 and ventricular portion 204 may expand and foreshorten to clamp the native valve annulus therebetween, with the prosthetic leaflets within the strut frame 205 opening and closing to allow blood to flow therethrough as the heart continues to beat. While in this position, the replacement valve may be subject to smaller forces upon contraction of the ventricle than would be experienced after the implantation is completed. In other words, because the inner shaft 226 is interposed between the prosthetic leaflets when the replacement valve is in the condition shown in FIGS. 2A-B, the prosthetic leaflets may not be able to fully close, resulting in smaller pressures than would be experienced by the replacement valve if the prosthetic leaflets were fully coapted during ventricular systole. Thus, despite the relatively low rigidity of ventricular portion 204, the replacement valve is unlikely to dislodge from the native valve annulus due to forces acting on the replacement valve while the inner shaft 226 is interposed between the prosthetic leaflets. For example, if a patient has a left ventricular systolic pressure of approximately 140 mm HG and a left atrial pressure of approximately 15 mm Hg, a fully closing valve may experience a pressure of 125 mm Hg. According to some examples, if the valve is held partially open by the nosecone 222 and/or the inner shaft 226, the pressure differential between the left ventricular and left atrium may be halved. Prior to removing the delivery device 220, the rigidity or stiffness of the replacement valve maybe increased to ensure that the replacement valve maintains proper positioning and function. The replacement valve may be separated from the deployment mechanism of delivery device once the rigidity or stiffness of the replacement valve has been increased such that the replacement valve may no longer rely on the nosecone 222 extending across the leaflets to prevent the ventricular portion from collapsing through the native valve annulus. According to some examples, the inner shaft 226 may cross the leaflets an angle off the centerline to hold the leaflets open thereby preventing the ventricular portion from collapsing through the native valve annulus. In such an example, the rigidity or stiffness of the replacement valve may be increased such that the replacement valve no longer relies on the inner shaft 226 to prevent the ventricular portion from collapsing through the native valve annulus. After the replacement valve is separated from the deployment mechanism of delivery device, the nosecone 222 may be retracted into abutment with the distal end of the outer sheath of the delivery device 220, and the delivery device 220 may be removed.

The wire deployment mechanism of delivery device 220 may include a delivery tube 224. The delivery tube 224 may extend from the delivery device 220. According to some examples, there may be a controller for use by a surgeon to advance the delivery tube 224 through the delivery device 220 and into the central opening of the replacement valve. The delivery tube 224 may be advanced through the central opening until delivery tube 224 abuts the first end 234 or second end 236 of guide channel 210. In some examples, the delivery tube 224 may be removably attached or coupled to the first or second end 234, 236 of guide channel 210. For example, the delivery tube 224 may be threadably coupled, magnetically coupled, connected via a snap lock mechanism, or any other coupling mechanism to guide channel 210. As shown in FIGS. 2A and 2B, the delivery tube 224 may be coupled to the second end 236 of guide channel 210. According to some examples, the delivery tube 224 may be coupled to guide channel 210 while the replacement valve is in a collapsed configuration within the delivery device. Delivery tube 224 may be coupled to guide channel 210 in any of the ways described above.

The delivery tube 224 may be made of polymer tubing. For example, the polymer tubing may be polyimide or PEBA. In some examples, the delivery tube 224 may be made of fabric. The fabric may be, for example, woven PET or ePTFE.

FIG. 2C illustrates a wire 230 being delivered to the guide channel 210 to increase the rigidity of the replacement valve. The wire 230 may be similar to a cardiac guidewire. For example, the wire 230 may be made of stainless steel, nitinol, titanium, or any other biocompatible metal. In some examples, the wire 230 may be coated with a lubricant or sleeve to reduce friction. Reducing friction may provide for easier advancement through the delivery device 220 and guide channel 210. According to some examples, the wire 230 may be tapered or shaped on its leading end. The taper may allow the wire 230 to track easily through a lumen or channel in the delivery device and the guide channel 210. The wire 230 may be advanced through the delivery device 220 and guide channel 210 via a pushing wire, not shown. For example, the wire 230 may be advanced from the inflow end of the replacement valve to the outflow end of the replacement valve until it enters guide channel 210. The pushing wire may abut the wire 230. In some examples, the pushing wire may be coupled to the wire 230 via a threaded interface. According to some examples, the pushing wire may be coupled to wire 230 via a snap lock, magnetic connection, or any other known coupling mechanisms.

Wire 230 may be advanced through delivery tube 224 and into guide channel 210 once delivery tube 224 is coupled to guide channel 210. The wire 230 may be pushed through delivery tube 224 and into guide channel 210 using a push wire (not shown). According to some examples, the wire 230 may be pre-shaped to the diameter of the replacement valve. The wire 230 may reside in a distal channel within the delivery device until it is pushed into guide channel 210. For example, the pusher wire may extend from a distal section of the delivery device out the back of the handle of the delivery device. The pusher wire may, according to some examples, have a handle for ease of use. The pusher wire may be pushed proximally to deploy the wire 230 into guide channel 210. The wire 230 may be a predefined length corresponding to the number of hoops that will be made within guide channel 210. As the wire 230 advances through guide channel 210, the wire 230 may increase the rigidity of the ventricular portion 204 of the replacement valve. For example, the wire 230 may create a hoop within guide channel 210. The rigidity of the ventricular portion may increase by the rigidity of the wire 230 hoop within guide channel 210. In some examples, a thicker or more rigid wire may be used to create even greater rigidity. If a large amount of additional rigidity is not needed to create the desired amount of retention force, a thinner or less rigid wire may be used to create the hoop.

According to some examples, the wire 230 may be pushed through guide channel 210 to create multiple hoops within guide channel 210. To create multiple hoops of wire within guide channel 210, delivery tube 224 may be retracted slightly before wire 230 completes the first hoop. Retracting delivery tube 224 may require uncoupling delivery tube 224 from guide channel 210. Retracting delivery tube 224 may allow wire 230 to span across space 232 as it is being pushed by the guidewire. Once wire 230 spans across space 232, the wire 230 may be able to create additional hoops in guide channel 210. In some examples, the guide channel 210 may be a spiral that makes multiple loops around the diameter of the replacement valve. In such an example, there may be no need to retract delivery tube 224 to create multiple hoops in guide channel 210. Each additional hoop of wire 230 may increase the rigidity of the ventricular portion 204. The greater rigidity in guide channel 210 may provide more retention force to keep the replacement valve from migrating once implanted. In some examples, a stiffer or more rigid wire 230 may be used. A stiffer or more rigid wire may be used so as to not have to create multiple hoops within guide channel 210. In some examples, a more rigid wire 230 may be used to create multiple hoops within guide channel 210 to provide even more rigidity in the ventricular portion 204. A less rigid wire 230 may be used for ease of delivery. When using a less rigid wire 230, more hoops may be needed to create the rigidity needed to prevent ventricular portion 204 from collapsing through the native valve.

FIG. 2D illustrates preparation for the removal of the delivery device. According to some examples, after the ventricular portion 204 reaches an adequate rigidity to prevent the ventricular portion 204 from collapsing through the native annulus, the ventricular portion 204 may be released from the deployment mechanism of the delivery device 220 such that the delivery device 220 may be removed. For example, once the ventricular portion reaches adequate rigidity, the replacement valve may have enough retention force to stay in place at hypertension pressure. The replacement valve may have adequate rigidity to stay in place at a pressure of 210 mm Hg. For example, if the orifice that the replacement valve fills is 36 mm in diameter, the area of the orifice would be 1018 mm^2. A pressure of 210 mm Hg is equivalent to 28 kPa (or 0.028 N/mm^2). Therefore, according to this example, the replacement valve would have to adequate rigidity to resist a 28N dislodgement force. As shown, a single hoop of wire 230 has been advanced through guide channel 210. The wire 230 may not create a complete hoop when inserted into guide channel 210. For example, wire 230 may only extend through guide channel 210 such that the ends of the wire 230 terminate at or near the first and second ends 234, 236 of guide channel 210. In some examples, wire 230 may extend across space 232 such that wire 230 create a substantially complete hoop. In such an example, the wire 230 may extend more than one hoop through guide channel 210 but not a complete second hoop. For example, wire 230 may begin at second end 236 of guide channel 210 but end or terminate at a point in guide channel 210 between first end 234 and second end 236 but not within space 232.

To prepare for removing delivery device 220, guide tube 224 may be retracted into delivery device 220. As illustrated in FIG. 2D, once the wire 230 is adequately advanced into guide channel 210 to create at least a partial loop, the guide tube 224 may be retracted into delivery device 220. According to some examples, the guide tube 224 may be uncoupled from guide channel 210 prior to retracting the guide tube 224. In examples where guide tube 224 abuts guide channel 210, guide tube 224 may be retracted without any additional steps.

Figure 2E:
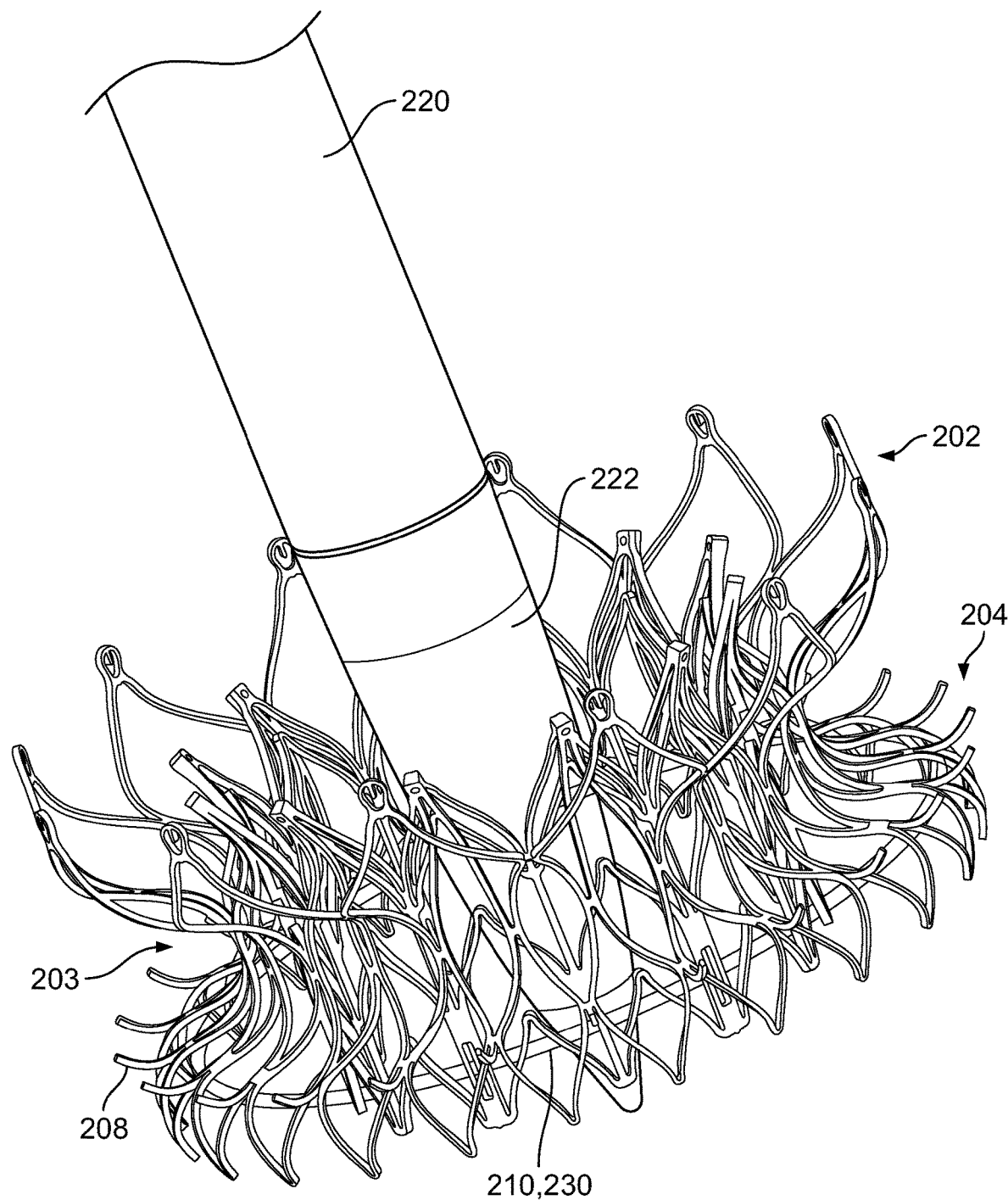
FIG. 2E illustrates a perspective view of the example deployment mechanism of the delivery device being removed from the stent according to aspects of the disclosure.

FIG. 2E illustrates an example of removing the delivery device 220 once the replacement valve and wire have been delivered. In some examples, the proximal end of nosecone 222 may be retracted into abutment with a distal end of the outer sheath of the delivery device 220. In such an example, inner shaft 226 may be retracted into delivery device 220 thereby retracting nosecone 222. The delivery device 220 is then retracted from the central portion of the replacement valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A replacement cardiac valve, comprising:
  a ventricular portion having a first stiffness, the ventricular portion formed of a super elastic material such that it is configured to self-expand from a collapsed configuration to an expanded configuration, the ventricular portion having a channel configured to receive a wire and extending substantially around a circumference of the ventricular portion, wherein the channel is a tubing and has a first end and a second end and forms a substantially circular shape comprising an incomplete circle having a C-shape defining a gap between the first end and the second end, wherein the channel is positioned on a luminal surface of the ventricular portion; and
  the wire configured to be advanced into the channel to increase the first stiffness to a second stiffness.

2. The replacement cardiac valve of claim 1, wherein when the wire is advanced into the channel, the wire forms at least one loop extending through the channel.

3. A replacement cardiac valve system including the replacement cardiac valve of claim 1, further comprising a delivery tube extending from a delivery device to a first end of the channel.

4. The replacement cardiac valve system of claim 3, wherein the wire is further configured to be advanced through the delivery tube and into the channel.

5. The replacement cardiac valve of claim 1, wherein when wrapped substantially around the circumference of the ventricular portion, the substantially circular shape a first diameter, the first diameter of the circle being greater than a second diameter of a native annulus.

6. The replacement cardiac valve of claim 1, wherein the ventricular portion further includes a fabric cover.

7. The replacement cardiac valve of claim 6, wherein the channel is integral with the fabric cover.

8. The replacement cardiac valve of claim 6, wherein the channel is a cuff coupled to the fabric cover.

9. The replacement cardiac valve of claim 1, wherein the ventricular portion includes a middle portion and an outflow end, the channel being located between the middle portion of the ventricular portion of the replacement cardiac valve and the outflow end.

10. The replacement cardiac valve of claim 1, wherein the ventricular portion includes a plurality of cells, the channel being located on a luminal surface of the plurality of cells.

11. The replacement cardiac valve of claim 1, wherein the tubing is a polymer.

12. A method of delivering a replacement cardiac valve having a collapsed configuration within a delivery device, the method comprising:
  delivering a ventricular portion having a first stiffness from the collapsed configuration in the delivery device to a first heart chamber on a first side of a mitral valve annulus, wherein the ventricular portion is formed of a super elastic material such that it self-expands to an expanded configuration on the first side of the mitral valve annulus, the ventricular portion configured to receive a wire and having a channel wrapping substantially around a circumference of the ventricular portion, wherein the channel is a tubing and has a first end and a second end and forms a substantially circular shape comprising an incomplete circle having a C-shape defining a gap between the first end and the second end, wherein the channel is positioned on a luminal surface of the ventricular portion; and during deployment of the replacement cardiac valve from the delivery device to the mitral valve annulus, advancing the wire into the channel of the ventricular portion, wherein the ventricular portion including the wire in the channel has a second stiffness that is increased relative to the first stiffness.

13. The method of claim 12, wherein advancing the wire into the channel comprises forming at least one loop extending through the channel.

14. The method of claim 12, further comprising advancing a delivery tube from the delivery device to connect the delivery tube to a first end of the channel.

15. The method of claim 14, wherein the delivery tube is removably coupled to the first end of the channel.

16. The method of claim 12, further comprising advancing a delivery tube from the delivery device to abut a first end of the channel.

17. The method of claim 12, wherein the channel has a first end and a second end, the first end being spaced from the second end.

18. The method of claim 12, wherein when wrapped substantially around the circumference of the ventricular portion, the channel creates a circle having a first diameter, the first diameter being greater than a second diameter of the mitral valve annulus.

19. The method of claim 12, wherein:

advancing the wire comprises pushing, using a push wire in the delivery device, the wire distally through the delivery device and into the channel, and the push wire is removably coupled to the wire.

20. The method of claim 12, wherein the wire is advanced into the channel while an atrial portion remains in the delivery device.

* * * * *